(12) United States Patent
Ishizaki et al.

(10) Patent No.: US 11,407,212 B2
(45) Date of Patent: Aug. 9, 2022

(54) PACKAGING MATERIAL AND PACKAGING STRUCTURE MADE BY USING SAME

(71) Applicant: Toyo Seikan Group Holdings, Ltd., Tokyo (JP)

(72) Inventors: Yoichi Ishizaki, Yokohama (JP); Yoshihiro Ohta, Yokohama (JP)

(73) Assignee: Toyo Seikan Group Holdings, Ltd., Tokyo (JP)

( * ) Notice: Subject to any disclaimer, the term of this patent is extended or adjusted under 35 U.S.C. 154(b) by 0 days.

(21) Appl. No.: 14/424,556

(22) PCT Filed: Sep. 24, 2013

(86) PCT No.: PCT/JP2013/075655
§ 371 (c)(1),
(2) Date: Feb. 27, 2015

(87) PCT Pub. No.: WO2014/046277
PCT Pub. Date: Mar. 27, 2014

(65) Prior Publication Data
US 2015/0258757 A1 Sep. 17, 2015

(30) Foreign Application Priority Data
Sep. 21, 2012 (JP) .............................. JP2012-208812

(51) Int. Cl.
| | |
|---|---|
| *B32B 27/36* | (2006.01) |
| *B32B 15/20* | (2006.01) |
| *B32B 27/08* | (2006.01) |
| *B32B 15/09* | (2006.01) |
| *A61F 13/00* | (2006.01) |
| *A61K 9/70* | (2006.01) |
| *B32B 7/12* | (2006.01) |
| *B65D 85/00* | (2006.01) |
| *A61K 8/02* | (2006.01) |

(52) U.S. Cl.
CPC ........ *B32B 27/36* (2013.01); *A61F 13/00076* (2013.01); *A61K 9/703* (2013.01); *B32B 15/09* (2013.01); *B32B 15/20* (2013.01); *B32B 27/08* (2013.01); *A61F 2013/00646* (2013.01); *A61F 2013/00655* (2013.01); *A61F 2013/00897* (2013.01); *A61F 2013/00906* (2013.01); *A61K 8/0208* (2013.01); *A61K 9/7023* (2013.01); *A61K 9/7038* (2013.01); *B32B 7/12* (2013.01); *B32B 2250/03* (2013.01); *B32B 2250/04* (2013.01); *B32B 2250/244* (2013.01); *B32B 2307/31* (2013.01); *B32B 2307/518* (2013.01); *B32B 2307/724* (2013.01); *B32B 2307/7242* (2013.01); *B32B 2311/24* (2013.01); *B32B 2367/00* (2013.01); *B32B 2439/80* (2013.01); *B32B 2556/00* (2013.01); *B65D 85/00* (2013.01); *Y10T 428/31565* (2015.04); *Y10T 428/31605* (2015.04); *Y10T 428/31681* (2015.04); *Y10T 428/31786* (2015.04)

(58) Field of Classification Search
None
See application file for complete search history.

(56) References Cited

U.S. PATENT DOCUMENTS

| | | | | |
|---|---|---|---|---|
| 4,562,779 | A * | 1/1986 | Briggs | A01B 73/044 111/173 |
| 4,765,999 | A * | 8/1988 | Winter | B32B 27/36 426/113 |
| 4,946,743 | A * | 8/1990 | Winter | B32B 27/08 428/349 |
| 5,085,904 | A * | 2/1992 | Deak | B32B 37/12 427/571 |
| 5,102,734 | A * | 4/1992 | Marbrow | B32B 27/08 428/349 |

(Continued)

FOREIGN PATENT DOCUMENTS

| | | |
|---|---|---|
| CN | 102218881 A | 10/2011 |
| EP | 1 097 809 A * | 5/2001 |

(Continued)

OTHER PUBLICATIONS

JP 60-048344 A (Takahashi) (published Mar. 16, 1985) English translation (1985) (Year: 1985).*
Office Action in CN Application No. 201380049093.0 dated Oct. 9, 2015.
Office Action in KR Application No. 9-5-2016-059665015 dated Aug. 19, 2016, 5 pages.
Search Report in International Application No. PCT/JP2013/075655 dated Jan. 7, 2014 (with translation).
Written Opinion in International Application No. PCT/JP2013/075655 dated Jan. 7, 2014.

* cited by examiner

*Primary Examiner* — Vivian Chen
(74) *Attorney, Agent, or Firm* — Marshall, Gerstein & Borun LLP

(57) ABSTRACT

The present invention provides a packaging material for a patch, the packaging material comprising: an inner layer film made of a polyethylene terephthalate-based resin having heat sealing properties; and a substrate film, wherein a heat-sealing surface of the inner layer film comprises an isophthalic acid-modified polyethylene terephthalate resin having a copolymerization ratio of isophthalic acid component of 10 mol % to 20 mol %. More preferably, the inner layer film made of the polyethylene terephthalate-based resin having heat sealing properties is a multi-layer film comprising at least two layers including a heat sealing surface side layer made of an isophthalic acid-modified polyethylene terephthalate resin having a copolymerization ratio of isophthalic acid component of 10 mol % to 20 mol % and a layer made of an isophthalic acid-modified polyethylene terephthalate resin having a copolymerization ratio of isophthalic acid component of 0 mol % to 5 mol %.

10 Claims, No Drawings

(56) References Cited

U.S. PATENT DOCUMENTS

| | | | | |
|---|---|---|---|---|
| 5,204,181 | A * | 4/1993 | Suzuki | B32B 15/08 428/349 |
| 5,747,174 | A * | 5/1998 | Kimura | B29C 55/023 428/480 |
| 5,912,307 | A * | 6/1999 | Paschke | B65D 1/0207 525/444 |
| 6,054,551 | A * | 4/2000 | Cornell | C08G 63/19 106/31.13 |
| 6,103,857 | A * | 8/2000 | Jones | C08G 63/199 528/271 |
| 6,489,386 | B1 * | 12/2002 | Plotzker | B65D 65/38 524/222 |
| 7,960,010 | B2 | 6/2011 | Kliesch | A01N 59/16 106/15.05 |
| 11,292,908 | B2 * | 4/2022 | Kawamura | C08L 23/0823 |
| 2001/0035593 | A1 * | 11/2001 | Peiffer | B29C 55/143 264/176.1 |
| 2002/0187328 | A1 * | 12/2002 | Murschall | C08J 5/18 428/220 |
| 2004/0219316 | A1 * | 11/2004 | Takahashi | B32B 15/08 428/35.7 |
| 2004/0236066 | A1 * | 11/2004 | Moore | C08G 63/183 528/308.1 |
| 2005/0074599 | A1 * | 4/2005 | Peiffer | B29C 55/023 428/323 |
| 2005/0100723 | A1 * | 5/2005 | Tanaka | B32B 27/08 428/220 |
| 2005/0170175 | A1 * | 8/2005 | Nichols | C08G 63/78 428/357 |
| 2005/0261462 | A1 * | 11/2005 | Nichols | C08G 63/80 528/272 |
| 2006/0127654 | A1 * | 6/2006 | Tanaka | B32B 27/36 428/212 |
| 2006/0275593 | A1 * | 12/2006 | Kern | B32B 27/08 428/220 |
| 2006/0286349 | A1 * | 12/2006 | Klein | B32B 27/08 428/141 |
| 2007/0059465 | A1 * | 3/2007 | Thompson | C08G 63/183 428/35.7 |
| 2008/0260917 | A1 * | 10/2008 | Sankey | B65D 81/34 426/114 |
| 2008/0274316 | A1 * | 11/2008 | Griffith | C08K 3/22 428/35.7 |
| 2009/0110888 | A1 * | 4/2009 | Wuest | B32B 27/28 428/200 |
| 2009/0123723 | A1 * | 5/2009 | Kliesch | A01N 59/16 428/220 |
| 2009/0131626 | A1 * | 5/2009 | Sheppard | C08G 63/183 528/272 |
| 2009/0187002 | A1 * | 7/2009 | Nichols | C08G 63/80 528/308.3 |
| 2010/0122927 | A1 * | 5/2010 | Matsuoka | B65D 75/366 206/438 |
| 2010/0247889 | A1 * | 9/2010 | Kliesch | C08J 7/065 428/220 |
| 2010/0280152 | A1 * | 11/2010 | Barhouse | B29C 48/08 523/523 |
| 2011/0091705 | A1 * | 4/2011 | Shih | B32B 27/36 428/220 |
| 2012/0090275 | A1 * | 4/2012 | Uchida | A61K 31/4045 53/473 |

FOREIGN PATENT DOCUMENTS

| | | | |
|---|---|---|---|
| JP | 55-166248 A | * | 12/1980 |
| JP | 60-048344 A | * | 3/1985 |
| JP | 62-222845 A | * | 9/1987 |
| JP | 02-171240 A | * | 7/1990 |
| JP | 2-277635 | | 11/1990 |
| JP | 3-270934 | | 12/1991 |
| JP | 5-305108 | | 11/1993 |
| JP | 7-108583 | | 4/1995 |
| JP | 8-20094 | | 1/1996 |
| JP | 9-39982 | | 2/1997 |
| JP | 09-039982 A | * | 2/1997 |
| JP | 2001-315284 | | 11/2001 |
| JP | 2001-315284 A | * | 11/2001 |
| JP | 2006-305975 | | 11/2006 |
| JP | 2006-305975 A | * | 11/2006 |
| JP | 4672429 B2 | | 4/2011 |
| KR | 20120024562 A | | 3/2012 |
| WO | WO 00/46026 A | * | 8/2000 |

PACKAGING MATERIAL AND PACKAGING STRUCTURE MADE BY USING SAME

TECHNICAL FIELD

The present invention relates to a packaging material for a patch, and particularly to a packaging material for a patch containing an oily component in an adhesive.

BACKGROUND ART

Patches, particularly transdermal patches having a drug in an adhesive layer are hermetically packaged with a sealed packaging material with the view to keeping the quality during storage or other purposes. However, there is such a problem that when a patch having an oily component in an adhesive is packaged with a packaging material, the oily component is adsorbed or transferred to the packaging material due to contact of the patch with the inner surface of the packaging material, which leads to change in the content of the oily component in the adhesive, and accordingly change in the adhesiveness. In addition, it has been pointed out that the transdermal patch has problems such as decreased transdermal absorption of a contained drug and decreased pharmacological effect due to the adsorption of the contained drug itself.

In order to address the above problems, it has been proposed that the inner surface of a packaging material is made of ethylene/vinyl alcohol copolymer or acrylonitrile/methyl acrylate copolymer (Japanese Patent Application Publication JP-A-5-305108). In addition, a packaging bag having a sealant layer made of an unstretched polyester has been proposed (Japanese Patent Application Publication JP-A-9-39982).

However, since the ethylene/vinyl alcohol copolymer or acrylonitrile/methyl acrylate copolymer is expensive, an alternative thereto has been demanded. Moreover, also when the unstretched polyester is used, the packaging material is required to have further improved performances, especially, to simultaneously achieve both the heat sealing properties and the non-absorbing properties at high levels.

SUMMARY OF INVENTION

Technical Problems

An object of the present invention is to provide a packaging material which prevents an oily component contained in an adhesive of a patch from being adsorbed or transferred to the packaging material, and which has excellent heat sealing characteristics.

Solution to Problems

The present invention provides a packaging material comprising: an inner layer film made of a polyethylene terephthalate-based resin having heat sealing properties; and a substrate film, wherein a heat-sealing surface of the inner layer film comprises an isophthalic acid-modified polyethylene terephthalate resin having a copolymerization ratio of isophthalic acid component of 10 mol % to 20 mol %.

In the packaging material of the present invention, it is preferable that:

(1) the inner layer film is a multi-layer film comprising at least two layers including a heat sealing surface side layer made of an isophthalic acid-modified polyethylene terephthalate resin having a copolymerization ratio of isophthalic acid component of 10 mol % to 20 mol % and a layer made of an isophthalic acid-modified polyethylene terephthalate resin having a copolymerization ratio of isophthalic acid component of 0 mol % to 5 mol %;

(2) the packaging material is a packaging material for a patch; and (3) the patch is a transdermal preparation in which an adhesive layer containing a transdermal drug is formed on one side of a support.

Furthermore, in a package structure of the present invention, it is preferable that:

(4) the package structure is a package structure having a patch packaged with the above-described packaging material; and (5) the patch is a transdermal preparation in which an adhesive layer containing a transdermal drug is formed on one side of a support.

Advantageous Effects of Invention

The present invention makes it possible to obtain a packaging material which prevents an oily component contained in an adhesive of a patch from being adsorbed or transferred to the packaging material, and which has excellent heat sealing characteristics.

DESCRIPTION OF EMBODIMENTS

A packaging material of the present invention comprises: an inner layer film made of a polyethylene terephthalate-based resin having heat sealing properties; and a substrate film, wherein a heat-sealing surface of the inner layer film comprises an isophthalic acid-modified polyethylene terephthalate resin having a copolymerization ratio of isophthalic acid component of 10 mol % to 20 mol %, preferably 12 mol % to 18 mol %, and particularly preferably 14 mol % to 16 mol %.

The isophthalic acid-modified polyethylene terephthalate resin having a copolymerization ratio of isophthalic acid component of 10 mol % to 20 mol % used as the polyethylene terephthalate-based resin having heat sealing properties is excellent in oily-component non-absorbing properties, and has excellent heat sealing properties. For this reason, the polyethylene terephthalate resin is excellent as a material for forming a heat-sealing surface of a packaging material by which an oily component in a patch can be prevented from being transferred to the packaging material. If the copolymerization ratio of isophthalic acid is less than 10 mol %, the heat sealing properties deteriorate due to crystallization during film formation. Meanwhile, if the copolymerization ratio exceeds 20 mol %, the non-absorbing properties deteriorate.

Moreover, the inner layer film made of the polyethylene terephthalate-based resin having heat sealing properties is particularly preferably a multi-layer film comprising at least two layers including a heat sealing surface side layer made of an isophthalic acid-modified polyethylene terephthalate resin having a copolymerization ratio of isophthalic acid component of 10 mol % to 20 mol %, preferably 12 mol % to 18 mol %, and particularly preferably 14 mol % to 16 mol % and a layer (i.e., a layer facing the substrate film) made of an isophthalic acid-modified polyethylene terephthalate resin having a copolymerization ratio of isophthalic acid component of 0 mol % to 5 mol %, preferably 0.1 mol % to 4 mol %, and particularly preferably 1 mol % to 3 mol %.

The polyethylene terephthalate having a relatively high degree of modification with a copolymerization ratio of isophthalic acid component of 10 mol % to 20 mol % has low crystallinity, and hence has excellent heat sealing characteristics and excellent non-absorbing properties. However, the polyethylene terephthalate having a low degree of modification with a copolymerization ratio of isophthalic acid component of 0 mol % to 5 mol % has higher non-absorbing properties. In addition, the polyethylene terephthalate with a low degree of modification is generally used in quantity as a material for PET bottles, and hence is available at low costs and is excellent in economic efficiency. Accordingly, when the inner layer film made of the polyethylene terephthalate-based resin has the above-described multi-layer structure, an inner layer film excellent in heat sealing characteristics, non-absorbing properties, and economic efficiency can be achieved.

It is also possible to add various additives to the inner layer film, unless the heat sealing characteristics and the non-absorbing properties are impaired. The additives include antioxidant, ultraviolet absorber, anti-hydrolysis agent, fungicide, curing catalyst, plasticizer, pigment, filler, lubricant, and the like.

The thickness of the inner layer film is preferably 10 µm to 30 µm, and particularly preferably 15 µm to 28 µm. If the thickness is above this range, the non-absorbing properties may deteriorate, or a problem of tearing properties may arise. Meanwhile, if the thickness is below this range, a problem of commercial value may arise because of decrease in the heat sealing strength or impairment of rigidity of the packaging material. When the inner layer film has the multi-layer structure, the thickness of the heat sealing surface side layer is preferably 2 to 20 µm, and particularly preferably 3 to 10 µm. The thickness of the layer of the polyethylene terephthalate having a low degree of modification can be set, as appropriate, so that the inner layer film can have a desired overall thickness, which includes the thickness of the heat sealing surface side layer. The thickness of the layer of the polyethylene terephthalate having a low degree of modification is preferably 10 to 28 µm, and particularly preferably 15 to 25 µm.

The inner layer film can be formed by a known film formation method such as T-die molding or inflation molding. Here, the film in a hot molten state is preferably solidified by rapid cooling. The rapid cooling inhibits the crystallization of the resin, so that a film excellent in heat sealing characteristics can be obtained.

In addition, the inner layer film is preferably in an unstretched state or in a state stretched with at a low draw ratio. Polyethylene terephthalate stretched at a high draw ratio is not preferable, because it loses the heat sealing properties due to oriented crystallization.

The substrate film is not particularly limited, and a film of biaxially stretched polyethylene terephthalate, biaxially stretched polyamide, or biaxially stretched polypropylene or the like can be used, because they are excellent in transparency, printability, chemical resistance, and strength. The thickness of the substrate film (excluding a gas barrier layer described later) is preferably 5 to 20 µm, and particularly preferably 10 to 15 µm.

Moreover, to prevent permeation of oxygen and steam, it is preferable to stack a gas barrier layer. An aluminum foil can be used as the gas barrier layer. The aluminum foil is suitably used, because it is excellent in not only barrier properties against oxygen and steam, but also light-shielding properties. When the gas barrier layer is stacked, the thickness is preferably 2 to 20 µm, and particularly preferably 5 to 10 µm.

For manufacture of the packaging material, a molding method known per se can be used. For example, a stacked body can be formed by extrusion molding with multiple multilayer dies using a certain number of extruders according to the resin types. The stacked body can be also manufactured by extrusion coating or sandwich lamination, or dry lamination of preformed films. For example, when the inner layer film made of a polyethylene terephthalate-based resin having heat sealing properties is formed in advance by a T-die method or the like as described above, the packaging material for a patch of the present invention can be obtained by stacking the inner layer film on a substrate film made of biaxially stretched polyethylene terephthalate by the dry lamination method.

The stacked body can be made into packaging bags such as general three-side or four-side sealed pouches, gusseted pouches, standing pouches, and pillow pouches. The bag-making can be carried out by well-known bag-makings.

The patch packaged with the above packaging material includes a support layer and an adhesive layer, in which a drug is included in the adhesive layer to treat or prevent various diseases through transdermal absorption of the drug. The drug here is not particularly limited, and both systemically acting drugs and locally acting drugs can be used. Examples of the drug include adrenocorticosteroids, non-steroid anti-inflammatory agents, antirheumatics, hypnotics, antipsychotics, antidepressants, mood stabilizers, psychostimulants, anxiolytics, antiepileptics, migraine medications, Parkinson's disease drugs, muscarinic receptor antagonists, restless legs syndrome drugs, cerebral circulation metabolism-improving agents, anti-dementia drugs, autonomic drugs, muscle relaxants, antihypertensives, diuretics, hypoglycemics, hyperlipemic drugs, gout drugs, general anesthetics, local anesthetics, antibiotics, antifungals, antivirotics, antiparasitics, vitamins, antianginals, vasodilators, antiarrhythmics, antihistamines, mediator release inhibitors, leukotriene antagonists, sexual hormones, thyroid hormones, antithyroids, antitumor agents, antiemetics, anti-vertigenous drugs, bronchodilators, antitussives, expectorants, stop smoking aids, and antiosteoporotic agents. These drugs may be used in a free form or may be used in a salt form. These drugs may be used alone or in a mixture of two or more.

The support layer is not particularly limited unless it is significantly uncomfortable to apply. Specifically, the support layer may be any of single films made of synthetic resins such as polyesters, polyolefins including polyethylene, polypropylene or the like, polyvinyl chloride, plasticized polyvinyl chloride, plasticized vinyl acetate-vinyl chloride copolymer, polyvinylidene chloride, ethylene-vinyl acetate copolymer, cellulose acetate, ethyl cellulose, ethylene-ethyl acrylate copolymer, polytetrafluoroethylene, polyurethane, and ionomer resins; laminate films thereof; porous films and sheets, nonwoven fabrics, and woven fabrics which are made of rubber, the above synthetic resins, polyesters such as polyethylene terephthalate, or polyamides such as nylon; laminates of these and the above synthetic resin film; and the like.

The patch is a transdermal preparation that preferably has the adhesive layer containing a transdermal drug formed on one side of the support. It may also have a release-treated release film which is stacked on the opposite side to the adhesive layer.

The patch is in a planar flat form, and the planar shape is any of, but is not limited to, substantial rectangle as well as polygons such as triangle and pentagon, i.e., shapes outlined with substantial straight lines, shapes outlined with a curve such as ellipse and circle, combination of these and the like.

The size of the patch can be appropriately selected according to the applications and applied parts of the patch and the like. For example, when the patch is substantially rectangle-shaped, the length of its one side is 15 to 90 mm and the length of the other side is also 15 to 90 mm.

The patch usually has a total thickness of 50 to 2000 μm and preferably has a total thickness of 100 to 1000 μm. While the patch includes the support layer and the adhesive layer, the support layer usually has a thickness of 1 to 1000 μm, and the adhesive layer usually has a thickness of 10 to 200 μm, and preferably has a thickness of 15 to 150 μm.

The adhesive layer may contain an oily component. The contained oily component plasticizes the adhesive layer to impart a soft feeling, reducing skin irritation, and controls the transdermal absorption of the drug. The oily component is preferably in a liquid form at room temperature (25° C.), and when a mixture of two or more of the oily components is used, it is preferably in a liquid form at room temperature (25° C.) at the end. Examples of the oily components include higher alcohols such as oleyl alcohol and octyldodecanol; polyhydric alcohols such as glycerol, ethylene glycol, and polypropylene glycol;

higher fatty acids such as caprylic acid and oleic acid; fatty acid esters such as isopropyl myristate, isopropyl palmitate, and ethyl oleate; polybasic acid esters such as diethyl sebacate and diisopropyl adipate; fatty acid esters of polyhydric alcohols, such as triisostearate diglyceryl, sorbitan monooleate, propylene glycol dicaprylate, polyethylene glycol monolaurate, and polyoxyethylene sorbitol tetraoleate; polyoxyethylene alkyl ethers such as polyoxyethylene lauryl ether; hydrocarbons such as squalane and liquid paraffin; vegetable oils such as olive oil and castor oil; silicone oils; pyrrolidones such as N-methylpyrrolidone and N-dodecylpyrrolidone; and sulfoxides such as decyl methyl sulfoxide. These oily components may be used alone or in a mixture of two or more.

The shape of the packaging body for the patch of the present invention is not particularly limited as long as the packaging body can package the patch. Examples of the shape include substantial rectangles such as square and rectangle, as well as polygons such as triangle and pentagon, circle, ellipse and other figures. The shape of the packaging body for a patch and the shape of the patch packaged may be the same or different as long as individual package (sealing) of the patch is achieved.

EXAMPLES

Hereinafter, the present invention is described more specifically based on Examples. The values were measured by the following methods.

(1) Heat Sealing Strength

Test pieces were fabricated by using a heat seal tester (manufactured by TESTER SANGYO CO,. LTD.) with a constant sealing time of 0.8 seconds and a constant sealing pressure of 2 kgf/cm$^2$, while the sealing temperature was varied, and the temperature at the seal interface was being measured. The heat sealing strength was measured according to JIS-Z1707 by using a high-precision universal testing machine Autograph AG-IS (manufactured by Shimadzu Corporation) under an environment of 23° C. and 50% RH. Each of the test pieces was pulled in the flow direction (MD) of the film at a rate of 300 mm/min, and the maximum testing force (N/15 mm) was taken as the heat sealing strength. A heat seal curve was prepared by plotting the heat sealing strength against the seal interface temperature. Here, the seal interface temperature at which the heat sealing strength reached 1 N/15 mm was taken as the seal expression temperature, and used for evaluation of the heat sealing characteristics, together with the heat sealing strength at a seal interface temperature of 110° C. Packaging materials satisfying both the conditions that the seal expression temperature was 90° C. or below and that the sealing strength at 110° C. was 15 N/15 mm or higher were considered to have good heat sealing characteristics.

(2) Oily-Component Non-Absorbing Properties

Test pieces of packaging materials in a size of 6 cm×10 cm were allowed to stand in an atmosphere of isopropyl myristate at 50° C. for 6 days, and then each test piece was subjected to extraction with 60 ml of hexane at 50° C. for 24 hours. Isopropyl myristate in the extraction liquid was quantitatively determined by gas chromatography. The result was expressed by a relative value, where the measurement result of the packaging material of Comparative Example 1 was taken as 100.

Example 1

A dry-laminate film of a 12 μm biaxially stretched polyethylene terephthalate (PET) film and a 7 μm aluminum foil was used as a substrate film, and a 25 μm unstretched bi-layer PET film of a 5 μm isophthalic acid-modified PET (with a copolymerization ratio of isophthalic acid component of 15 mol %) and a 20 μm isophthalic acid-modified PET (with a copolymerization ratio of isophthalic acid component of 2 mol %) was used as an inner layer film. With the aluminum foil of the substrate film and the 20 μm isophthalic acid-modified PET (with a copolymerization ratio of isophthalic acid component of 2 mol %) of the inner layer film facing each other, the substrate film and the inner layer film were stacked on each other by the dry lamination method using a two-part curing urethane-based adhesive agent to obtain a packaging material. Table 1 shows the evaluation results of the obtained packaging material.

Comparative Example 1

A packaging material was obtained in the same manner as in Example 1, except that a 30 μm LDPE film (AJ-3 manufactured by TAMAPOLY CO., LTD.) was used as the inner layer film. Table 1 shows the evaluation results.

Comparative Example 2

A packaging material was obtained in the same manner as in Example 1, except that a 30 μm PAN film (HIGHTORON BX manufactured by TAMAPOLY CO., LTD.) was used as the inner layer film. Table 1 shows the evaluation results.

Comparative Example 3

A packaging material was obtained in the same manner as in Example 1, except that a 25 μm unstretched single-layer isophthalic acid-modified PET (with a copolymerization ratio of isophthalic acid component of 2 mol %) was used as the inner layer film. Table 1 shows the evaluation results.

Comparative Example 4

A packaging material was obtained in the same manner as in Example 1, except that a 25 μm unstretched single-layer isophthalic acid-modified PET (with a copolymerization ratio of isophthalic acid component of 5 mol %) was used as the inner layer film. Table 1 shows the evaluation results.

TABLE 1

| | Heat sealing characteristics | | | Non-absorbing properties | | |
|---|---|---|---|---|---|---|
| | Seal expression temperature | Sealing strength (110° C.) | Evaluation | Amount of isopropyl myristate absorbed | Evaluation | Overall evaluation |
| Example 1 | 90° C. | 21N/15 mm | ○ | <0.1 | ○ | ○ |
| Comp. Ex. 1 | 88° C. | 27N/15 mm | ○ | 100 | x | x |
| Comp. Ex. 2 | 102° C. | 3N/15 mm | x | 1.8 | x | x |
| Comp. Ex. 3 | 100° C. | 13N/15 mm | x | <0.1 | ○ | x |
| Comp. Ex. 4 | 98° C. | 15N/15 mm | x | <0.1 | ○ | x |

The invention claimed is:

1. A packaging material for a transdermal patch containing isopropyl myristate, the packaging material comprising:
    an inner layer film consisting essentially of polyethylene terephthalate-based resin having heat sealing properties; and
    a substrate film, wherein:
    the inner layer film is a multi-layer film consisting essentially of at least two resin layers including:
        (a) a heat sealing surface side layer consisting essentially of a first isophthalic acid-modified polyethylene terephthalate resin containing only ethylene terephthalate units and modifying isophthalate units, wherein the first isophthalic acid-modified polyethylene terephthalate resin has a copolymerization ratio of isophthalate units of 10 mol % to 20 mol %, and
        (b) a substrate film side layer adjacent to the heat sealing surface side layer consisting essentially of a second isophthalic acid-modified polyethylene terephthalate resin containing only ethylene terephthalate units and modifying isophthalate units, wherein the second isophthalic-acid modified polyethylene terephthalate resin has a copolymerization ratio of isophthalate units of 0.1 mol % to 5 mol %,
    the heat sealing surface side layer and the substrate film side layer are both unstretched,
    the thickness of the heat sealing surface side layer is from above 2 μm to 5 μm,
    the thickness of the substrate film side layer is 10 μm to 28 μm,
    the packaging material exhibits a heat sealing strength at 110° C. measured according to JIS-Z1707 of at least 15 N/15 mm; and,
    the packaging material exhibits a rate of isopropyl myristate absorption of less than 0.1% of a 30 μm LDPE film under the same conditions.

2. The packaging material according to claim 1, wherein the transdermal patch is a transdermal preparation in which an adhesive layer containing a transdermal drug and isopropyl myristate is formed on one side of a support.

3. A package structure having a transdermal patch packaged with the packaging material according to claim 1.

4. The package structure according to claim 3, wherein the transdermal patch is a transdermal preparation in which an adhesive layer containing a transdermal drug and isopropyl myristate is formed on one side of a support.

5. The packaging material according to claim 1, wherein the thickness of the heat sealing surface side layer is from 3 μm to 5 μm.

6. The packaging material according to claim 1, wherein the copolymerization ratio of isophthalate units of the second isophthalic acid-modified polyethylene terephthalate resin is 0.1 mol % to 4 mol %.

7. The packaging material according to claim 1, wherein:
    the transdermal patch is a transdermal preparation in which an adhesive layer containing a transdermal drug and isopropyl myristate is formed on one side of a support,
    the thickness of the heat sealing surface side layer is from 3 μm to 5 μm, and
    the copolymerization ratio of isophthalate units of the second isophthalic acid-modified polyethylene terephthalate resin is 0.1 mol % to 4 mol %.

8. A package structure having a transdermal patch packaged with the packaging material according to claim 7.

9. The packaging material according to claim 1, wherein the substrate film comprises a biaxially-stretched polyethylene terephthalate film and an aluminum foil, with the aluminum foil facing the substrate film side layer of the inner layer film.

10. The packaging material of claim 1, wherein the substrate film and the inner layer film are laminated by use of a two-part curing urethane-based adhesive agent.

* * * * *